(12) United States Patent
Huh (10) Patent No.: US 8,457,949 B2
(45) Date of Patent: Jun. 4, 2013

(54) METHOD FOR DISPLAYING INFORMATION IN MULTIPLE LANGUAGES ON WELDING HELMET CARTRIDGE

(75) Inventor: Moon Young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 485 days.

(21) Appl. No.: 12/840,359

(22) Filed: Jul. 21, 2010

(65) Prior Publication Data

US 2011/0251838 A1    Oct. 13, 2011

(30) Foreign Application Priority Data

Apr. 13, 2010   (KR) .................. 10-2010-0033859

(51) Int. Cl.
*G06F 17/20* (2006.01)

(52) U.S. Cl.
USPC ........................................ 704/8; 2/8.2; 351/44

(58) Field of Classification Search
USPC ......................................... 707/8; 2/8; 351/44
See application file for complete search history.

(56) References Cited

U.S. PATENT DOCUMENTS

| | | | |
|---|---|---|---|
| 5,533,206 A | 7/1996 | Petrie et al. | |
| 6,070,264 A | 6/2000 | Hamilton et al. | |
| 6,151,711 A * | 11/2000 | Edwards | 2/8.3 |
| 6,796,496 B2 * | 9/2004 | Andersen et al. | 235/380 |
| 7,264,151 B2 * | 9/2007 | Im | 235/379 |
| 7,320,110 B2 * | 1/2008 | Shah | 715/764 |
| 2004/0210976 A1 * | 10/2004 | Huh | 2/8 |
| 2004/0243940 A1 * | 12/2004 | Lee et al. | 715/744 |
| 2006/0136220 A1 * | 6/2006 | Gurram et al. | 704/275 |
| 2008/0092259 A1 * | 4/2008 | Seo | 2/12 |
| 2008/0158502 A1 * | 7/2008 | Becker et al. | 351/44 |

* cited by examiner

*Primary Examiner* — Jialong He (74) *Attorney, Agent, or Firm* — Cantor Colburn LLP (57) ABSTRACT

A method for displaying information in multiple languages on a welding helmet cartridge is provided, which not only shields a worker's face from light generated when the worker performs a task such as welding or cutting but also automatically performs shade level adjustment and work time setting functions for each task and also allows information such as an operating status to be displayed in multiple languages. In the method, a work time during which the LCD screen of the cartridge is darkened is calculated and the calculated work time is stored in the memory and the stored work time is displayed on the display unit when entering a life mode entrance step. Data of an operating state in multiple preset languages is stored in the memory and data of the operating state in a desired language, which is selected from among the multiple languages, is displayed on the display unit.

6 Claims, 8 Drawing Sheets

METHOD FOR DISPLAYING INFORMATION IN MULTIPLE LANGUAGES ON WELDING HELMET CARTRIDGE

BACKGROUND OF THE INVENTION

1. Field of the Invention

The present invention relates to a method for displaying information in multiple languages on a welding helmet cartridge, and more particularly to a method for displaying information in multiple languages on a welding helmet cartridge, which not only shields a worker's face from light generated when the worker performs a task such as welding or cutting but also automatically performs shade level adjustment and work time setting functions for each task and also allows information such as an operating status, a user manual, and relevant terms to be displayed in multiple languages on a screen of the cartridge.

2. Description of the Related Art

Generally, arc welding involves locally heating and melting metals using fusibility of metals to join the metals together. The worker puts on a welding helmet as protective equipment for protecting the worker from high heat, light, and gas generated during welding.

A conventional welding helmet having a handle causes inconvenience since the welder should perform specific actions a number of times when using the welding helmet, for example, they should often hold and release the handle each time they raise and lower the welding helmet to perform welding.

The welding helmet has been researched and developed into a bend helmet to improve task efficiency of the worker.

Especially, the welding helmet is used to protect the worker's eyes and face when performing tasks such as welding or cutting. An anti-glare device, which will hereinafter be referred to as a "cartridge", is fixedly mounted to the welding helmet to protect the user's eyes from intense harmful light generated when performing tasks such as welding or cutting.

Such a cartridge generally shields light of greater than 780 nm (IB) and less than 365 nm (UV) and controls the transmittance of visible light to allow the user to perform work while viewing welding locations without exposure to intense.

U.S. Pat. No. 5,533,206 describes a welding helmet including an electronic quick change (EQC) cartridge and a cartridge housing. The EQC cartridge includes a Liquid Crystal Display (LCD) lens, solar cells, and photo sensor cells. The LCD lens is positioned directly in front of the eyes of the wearer, thereby functioning as the actual viewing window. The solar cells absorb light and function as an energy input unit. The photo sensor cells detect sparks and other intense light and act as an input to a circuit that automatically adjusts the LCD lens to a variable opaque condition. The cartridge housing is located in the helmet in order to fixedly mount the EQC cartridge to the helmet.

In addition, U.S. Pat. No. 6,070,264 describes a welding helmet including a shutter, a light sensor, and an electronic circuit. The shutter is mounted such that the helmet's wearer can view a welding operation. The electronic control is coupled to the shutter to control a light transmission shade of the shutter. The light sensor detects light emitted from the welding operation. The electronic circuit drives the shutter to a darker shade in response to the light sensor sensing brighter light from the welding operation.

However, since information such as information as to how to manipulate (or operate) the welding helmet is displayed on the welding helmet only in English or in a language of a specific country, the conventional welding helmet has a problem in that it is not easy for welders from other countries to read such information.

In addition, since welding helmets for use in each specific country should be manufactured for the language of the specific country, manufacturing time and costs are increased. It also takes a long time for foreign workers to learn how to use the welding helmet since the welding helmet does not display such information in their own language when they use the welding helmet.

SUMMARY OF THE INVENTION

Therefore, the present invention has been made in view of the above problems, and it is an object of the present invention to provide a method for displaying information in multiple languages on a welding helmet cartridge, which not only shields a worker's face from light generated when the worker performs a task such as welding or cutting but also automatically performs shade level adjustment and work time setting functions for each task and also allows information such as an operating status, a user manual, and relevant terms to be displayed in multiple languages on the cartridge.

It is another object of the present invention to provide to provide a method for displaying information in multiple languages on a welding helmet cartridge, which recognizes voice of a user to determine the user's own language so that the welding helmet cartridge displays operating states (or task information) in the user's own language without manual control by the user.

In accordance with the present invention, the above and other objects can be accomplished by the provision of a method for controlling a cartridge of a welding helmet that sequentially performs a welding step, a cutting step, a grinding step, and an X-mode step automatically according to a preset condition, a shade level of an LCD screen, and an operating time of the cartridge, the cartridge including the LCD screen, a display unit, a controller, and a memory, the method including calculating, by the controller, a work time during which the LCD screen of the cartridge is darkened and storing the calculated work time in the memory and displaying the stored work time on the display unit when entering a life mode entrance step, and storing data of an operating state in multiple preset languages in the memory and displaying data of the operating state in one language, which the controller has selected from among the multiple languages, on the display unit.

The cartridge may further include a voice recognition unit for recognizing voice of a user, wherein the controller determines a language recognized by the voice recognition unit and selects data of an operating state of the recognized language stored in the memory and displays the data of the operating state of the recognized language on the display unit.

The method according to the present invention has a variety of advantages. For example, the cartridge not only shields a worker's face from light generated when the worker performs a task such as welding or cutting but also automatically performs shade level adjustment and work time setting functions for each task, and also allows information such as an operating status, a user manual, and relevant terms to be displayed in multiple languages on the cartridge, thereby increasing convenience of task. While all welding helmet cartridges are currently designed to display task information in English, the present invention eliminates the need to design welding helmet cartridges which display task information in the language of each country to which the welding helmet cartridges are exported. In addition, non-English speaking workers in the United States can select their own language for display of task information when using the welding helmet cartridges.

In addition, the cartridge recognizes voice of a user to determine the user's own language so that the welding helmet cartridge displays operating states (or task information) in the user's own language without manual control by the user.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Preferred embodiments of the present invention will now be described in detail with reference to the accompanying drawings.

Prior to the description, it should be noted that the terms and words used in the present specification and claims should not be construed as being limited to common or dictionary meanings but instead should be understood to have meanings and concepts in agreement with the spirit of the present invention based on the principle that an inventor can define the concept of each term suitably in order to describe his/her own invention in the best way possible. Thus, the embodiments described in the specification and the configurations shown in the drawings are simply the most preferable examples of the present invention and are not intended to illustrate all aspects of the spirit of the present invention. As such, it should be understood that various equivalents and modifications can be made to replace the examples at the time of filing of the present application. Wherever possible, the same reference numbers will be used throughout the drawings to refer to the same or like parts.

Figure 1:
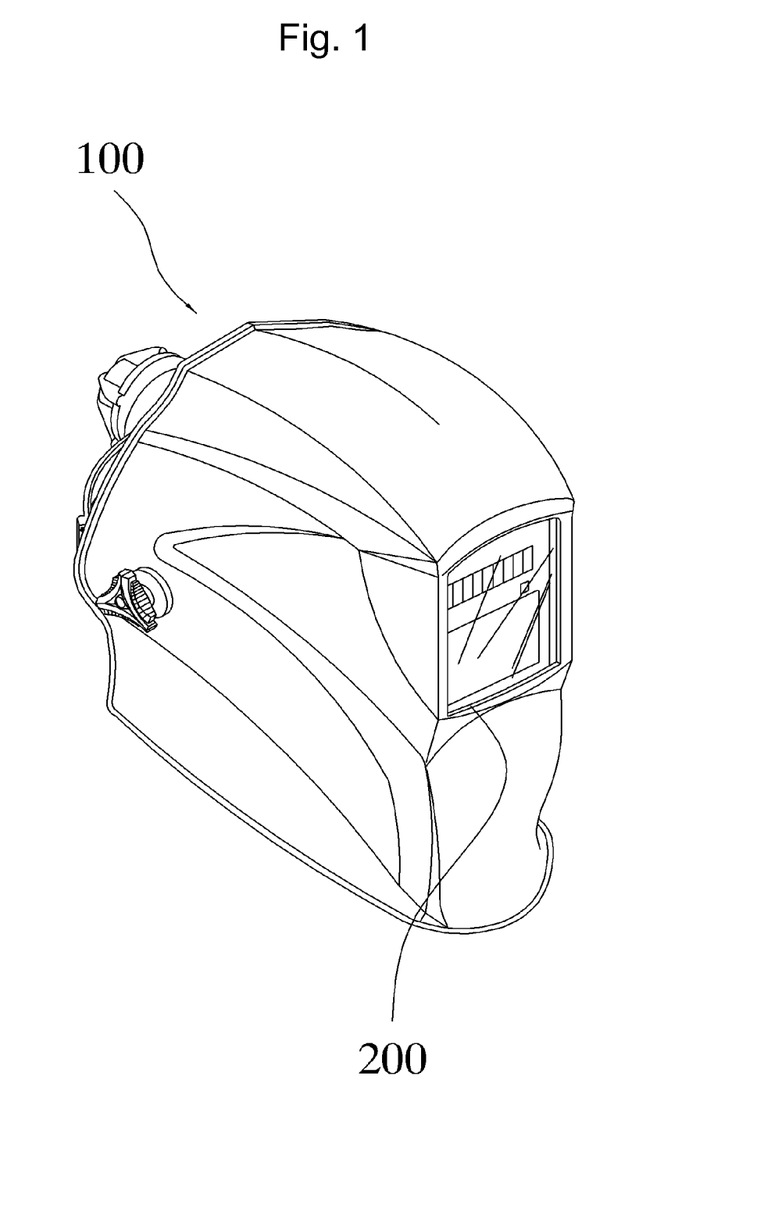
FIG. 1 illustrates a welding helmet according to the present invention.
Figure 2:
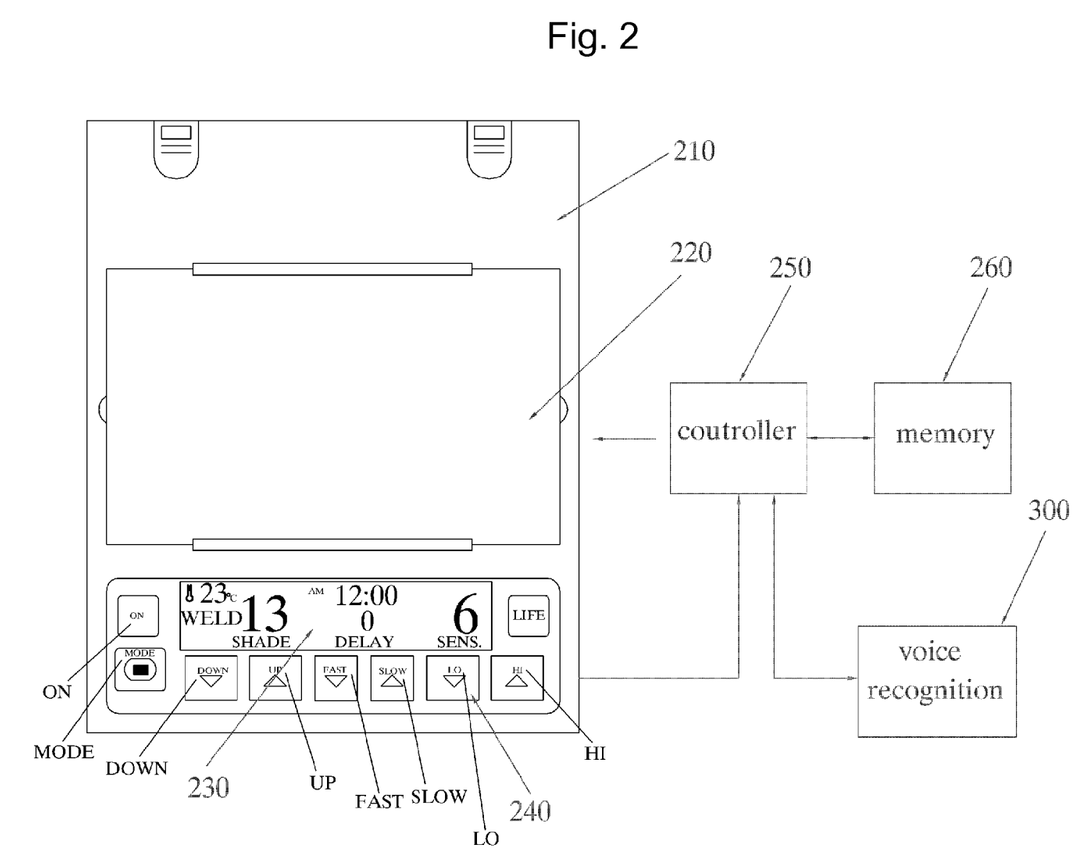
FIG. 2 is a block diagram illustrating details of the cartridge of FIG. 1 for implementing a method for displaying information in multiple languages on a welding helmet cartridge according to the present invention.

FIG. 1 illustrates a welding helmet according to the present invention and FIG. 2 is a block diagram illustrating details of the cartridge of FIG. 1 for implementing a method for displaying information in multiple languages on a welding helmet cartridge according to the present invention.

As shown in FIGS. 1 and 2, the welding helmet 100 of the present invention includes a cartridge 200, which includes a body 210, an LCD screen 220, a display unit 230, a key input unit 240, a controller 250, a memory 260, and a voice recognition unit 300.

The welding helmet 100 is formed so as to protect and cover the worker's face and the cartridge 200 is mounted to the front side of the welding helmet 100.

Material of the welding helmet 100 preferably includes a light substance such as nonflammable plastic.

The body 210 of the cartridge 200 defines the external shape of the cartridge 200 and the controller 250, which includes a general microcomputer, and the memory 260 are provided in the body 210.

The LCD screen 220 changes its shade level according to manual control by the user or according to control of the controller. First, the worker puts on the welding helmet 100 to cover his/her face and then performs a welding or cutting task with appropriate brightness through the LCD screen 220.

The display unit 230 displays input states of the user, operating states of the device, or the like.

The key input unit 240 receives and transfers a command from the user to the controller 250.

The controller 250 controls the overall operation of the device and the memory 260 stores key input values and data values according to the operating states.

The memory 260 may store data of operating states in multiple preset languages and the display unit 230 may display data of the operating states in one language that the controller 250 has selected from among the multiple languages.

The voice recognition unit 300 recognizes voice of the user.

Here, the controller 250 may determine a language recognized by the voice recognition unit 300 and select data of the operating states corresponding to the determined language from among the data of the operating states of the multiple languages and then display the selected operating state data on the display unit 230.

The following is a more detailed description of the operation of the present invention.

Figure 3:
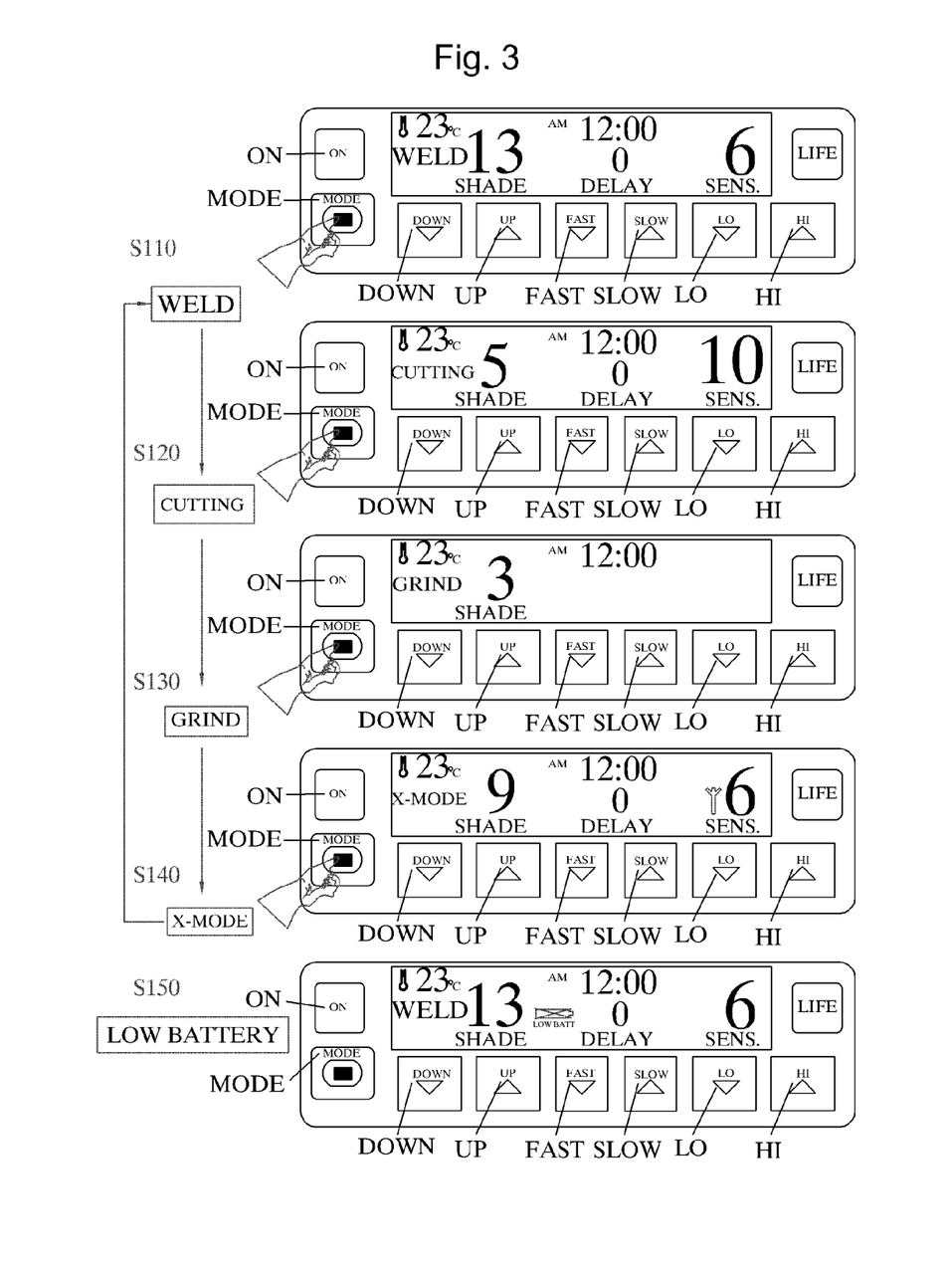
FIG. 3 illustrates a procedure for adjusting the shade level of the LCD screen for each task in a method for controlling the cartridge of the welding helmet according to the present invention.

FIG. 3 illustrates a method for controlling the cartridge of the welding helmet according to the present invention. Specifically, FIG. 3 illustrates a procedure for adjusting the shade level of the LCD screen 220 for each task.

According to the present invention, the controller 250 may sequentially perform a welding step S110, a cutting step S120, a grinding step S130, and an X mode step S140 automatically according to a preset condition, the shade level of the LCD screen 220, and the operating time of the cartridge.

Here, the controller 250 detects voltage of a battery of the cartridge 200 and performs, when the voltage is low, a low voltage warning step S150 to display a low voltage status on the display unit 230.

Especially, the memory 260 may store data of operating states in multiple preset languages and the display unit 230 may display data of the operating states in one language that the controller 250 has selected from among the multiple languages.

In one embodiment, the memory 260 stores data of operating states in multiple languages and other data such as a user manual. Examples of the multiple languages include Korean, English, French, German, Italian, Chinese, Japanese, Russian, Arabic, Greek, Brazil, Thai, and Vietnamese.

Accordingly, the user may previously select a language for use by operating command keys on the key input unit 240 so that data of the selected language is displayed on the display unit 230. Thus, the user can conveniently perform a task while viewing the displayed operating state in his/her language even when the user does not know various languages.

In another embodiment, the voice recognition unit 300 may recognize voice of the user.

For example, when the user says the word "Korean", "English", or "Nihongo", the voice recognition unit 300 recognizes and transfers the word to the controller 250 and the controller 250 determines a language corresponding to the word recognized by the voice recognition unit 300.

The controller 250 selects data of the operating states corresponding to the determined language from among the data of the operating states in multiple languages stored in the memory 260 and displays the selected operating state data on the display unit 230.

Thus, the welding helmet cartridge according to the present invention can recognize voice of the user to determine the user's own language and can display operating states (or task information) in the user's own language without manual control by the user.

Figure 4:
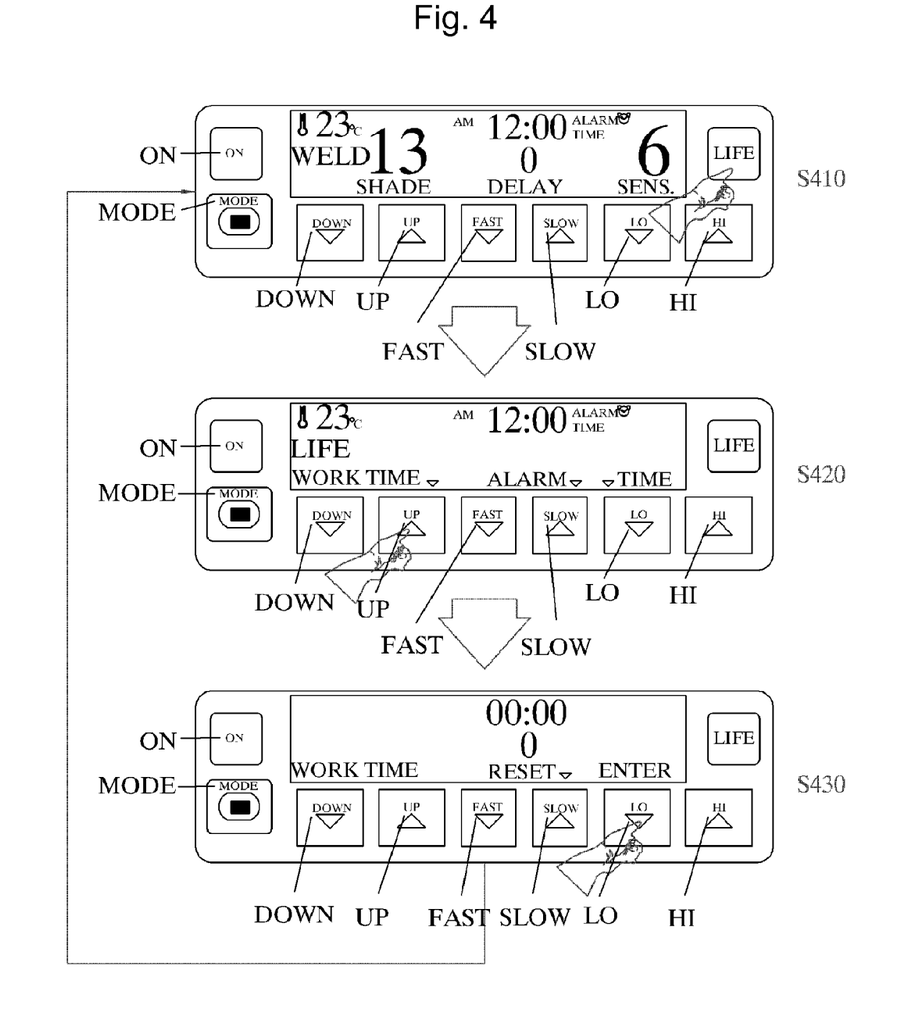
FIG. 4 illustrates a work time setting procedure according to the present invention.

FIG. 4 illustrates a work time setting procedure according to the present invention.

When the user presses a "LIFE" button at step S210, the controller 250 enters a life mode entrance step S220. At the life mode entrance step S220, the user may select a 12/24 time mode (12 or 24-hour clock) selection item, a Fahrenheit/Celsius selection item, an alarm adjustment item, and a time adjustment item (for example, an alarm time adjustment item). Here, when the user selects the alarm adjustment item, the controller 250 proceeds to an (alarm) time setting step S230 at which the user adjusts hour and minute values and then presses an enter key at a time setting completion step 240 to complete time setting. When the user has selected the time adjustment item at the life mode entrance step S220, the controller 250 proceeds to a time adjustment step S250 at which the user adjusts hour and minute values and then presses an enter key at the time setting completion step 240 to complete time adjustment.

Figure 5:
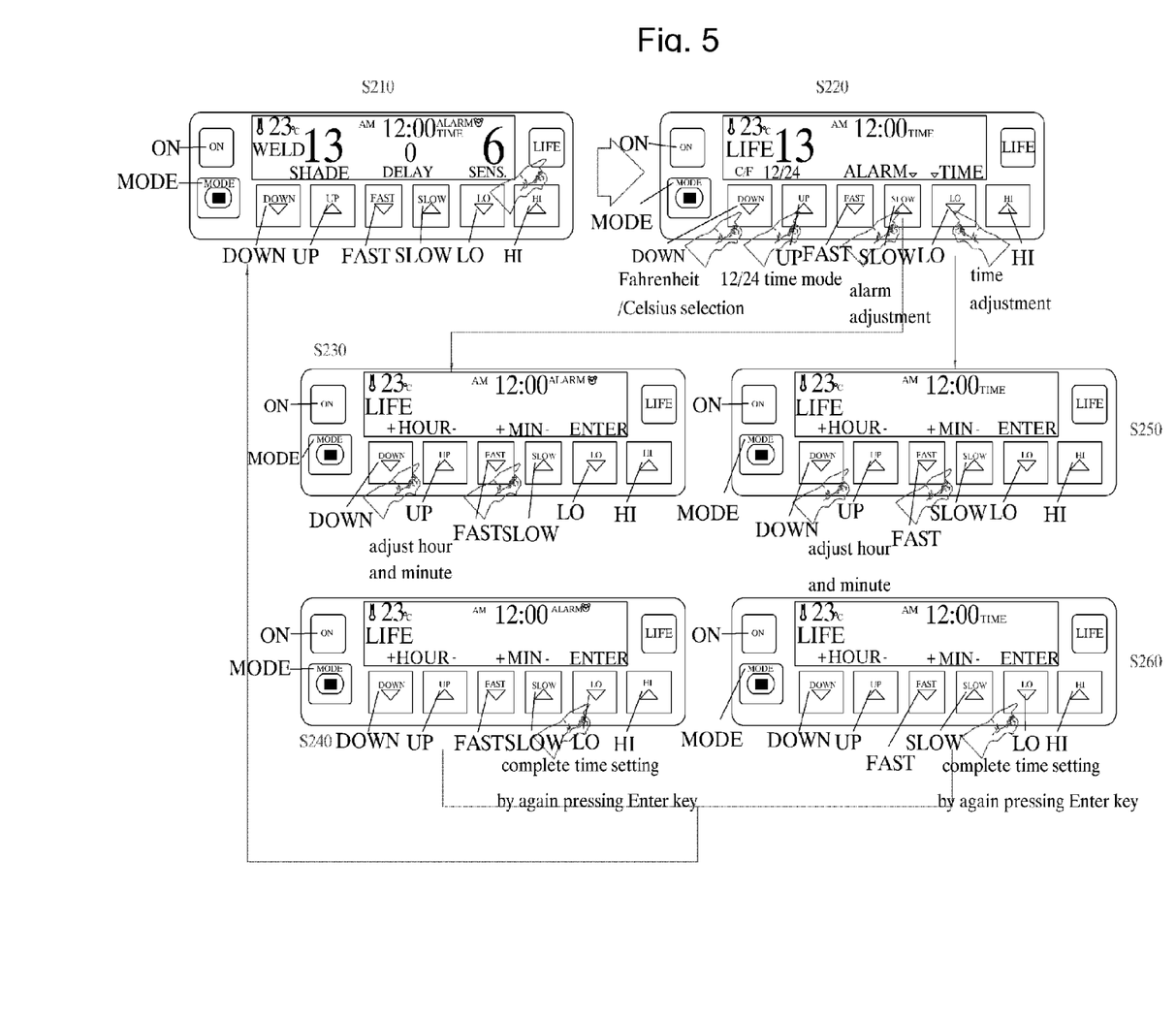
FIG. 5 illustrates an alarm time cancelation procedure according to the present invention.

FIG. 5 illustrates an alarm time cancelation procedure according to the present invention.

When the user presses the "LIFE" button at an initial step S310, the controller 250 enters an alarm adjustment step S320 at which the user sets alarm details. Then, when the user selects alarm cancelation at an alarm cancelation step S330, the alarm is canceled and then an alarm cancelation completion step S340 is finished.

Figure 6:
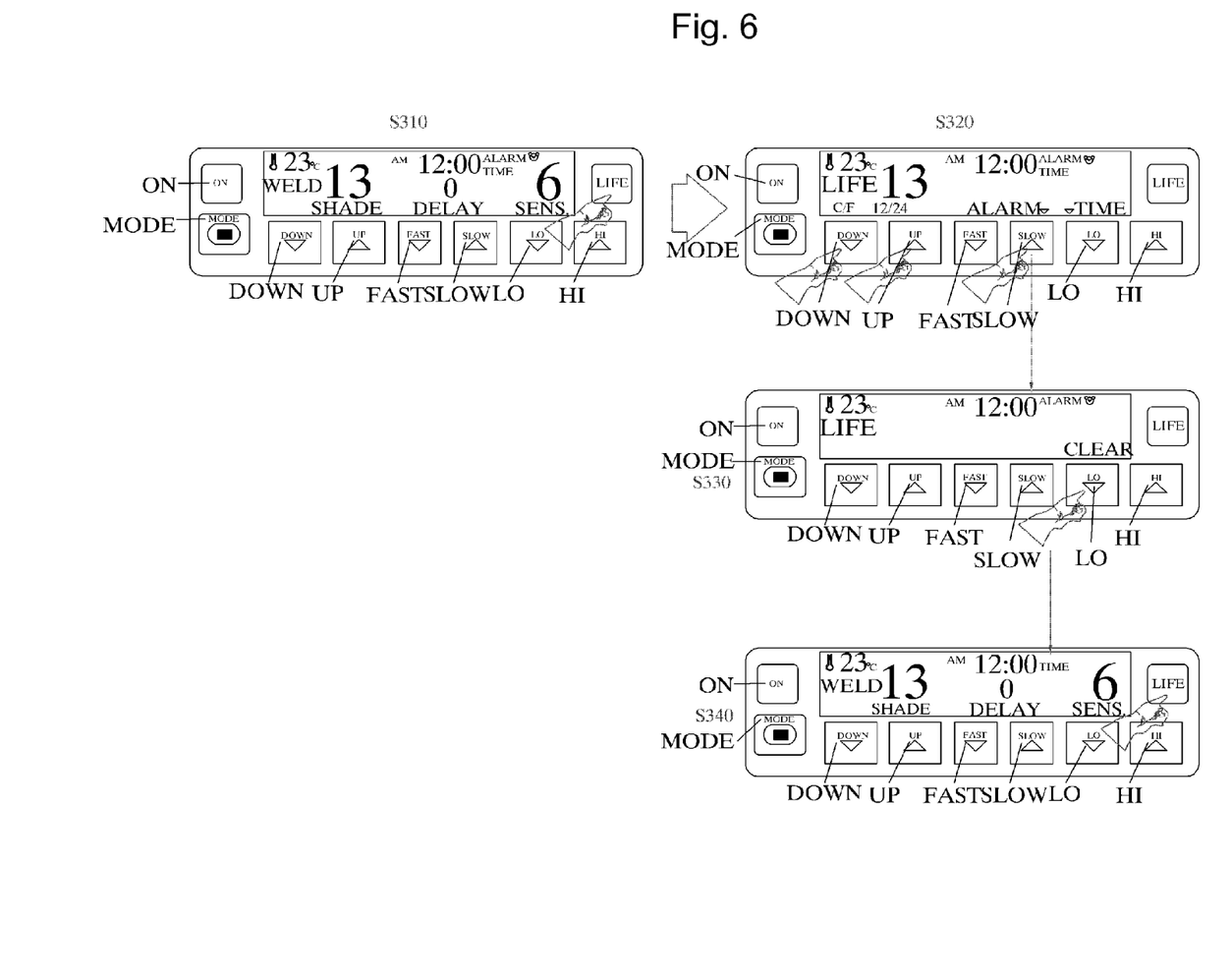
FIG. 6 illustrates a work time display procedure according to the present invention.

FIG. 6 illustrates a work time display procedure according to the present invention.

In the work time display procedure according to the present invention, the controller 250 sequentially performs a work time mode entrance step S410, a work time setting step S420, and a work time setting completion step S430. At the work time mode entrance step S410, the controller 250 calculates a work time during which the LCD screen 220 of the cartridge 200 is darkened and stores the calculated work time in the memory 260 and displays the stored work time on the display unit 230 when entering the life mode.

The display unit 230 displays a work time of up to 99 hours and 60 minutes. The work time is reset upon battery change. For example, when the work time has reached 99 hours and 60 minutes, the work time stops increasing after a warning message is issued. Here, the work time can be reset only by the user.

Preferably, the display unit 230 displays time in units of minutes.

The temperature unit (Fahrenheit/Celsius) displayed on the display unit 230 may be fixedly set to Fahrenheit and the time mode (12/24) displayed on the display unit 230 may be fixedly set to 12 hours.

In a method of displaying a work time in a real manner or in real time, high power consumption is required since the temperature value is displayed in 4 digits on the display unit 230 (for example, an LCD display unit) and the display unit 230 always operates to display (work time) data when blackening is finished.

Accordingly, in the present invention, when the cartridge enters the life mode, the (LCD) display unit 230 may be brought into an optimal display state to display the work time so that the user can immediately view the work time.

In the present invention, at the welding step S110, the cutting step S120, the grinding step S130, and the X mode step S140, the controller 250 may calculate a work time of each step and display the work time on the display unit 230 to allow the user to view the work time of each step.

Here, at the cutting step S120 and the grinding step S130, the cartridge 200 internally detects light during the task and calculates (or measures) a non-work time of the worker during which the worker does not work. However, a small error may occur in calculation of the non-work time since light is weak during the task such as grinding or cutting is actually performed. Accordingly, the present invention may avoid such an error by increasing an allowable error range when calculating the work time at each of the cutting step S120 and the grinding step S130.

Figure 7:
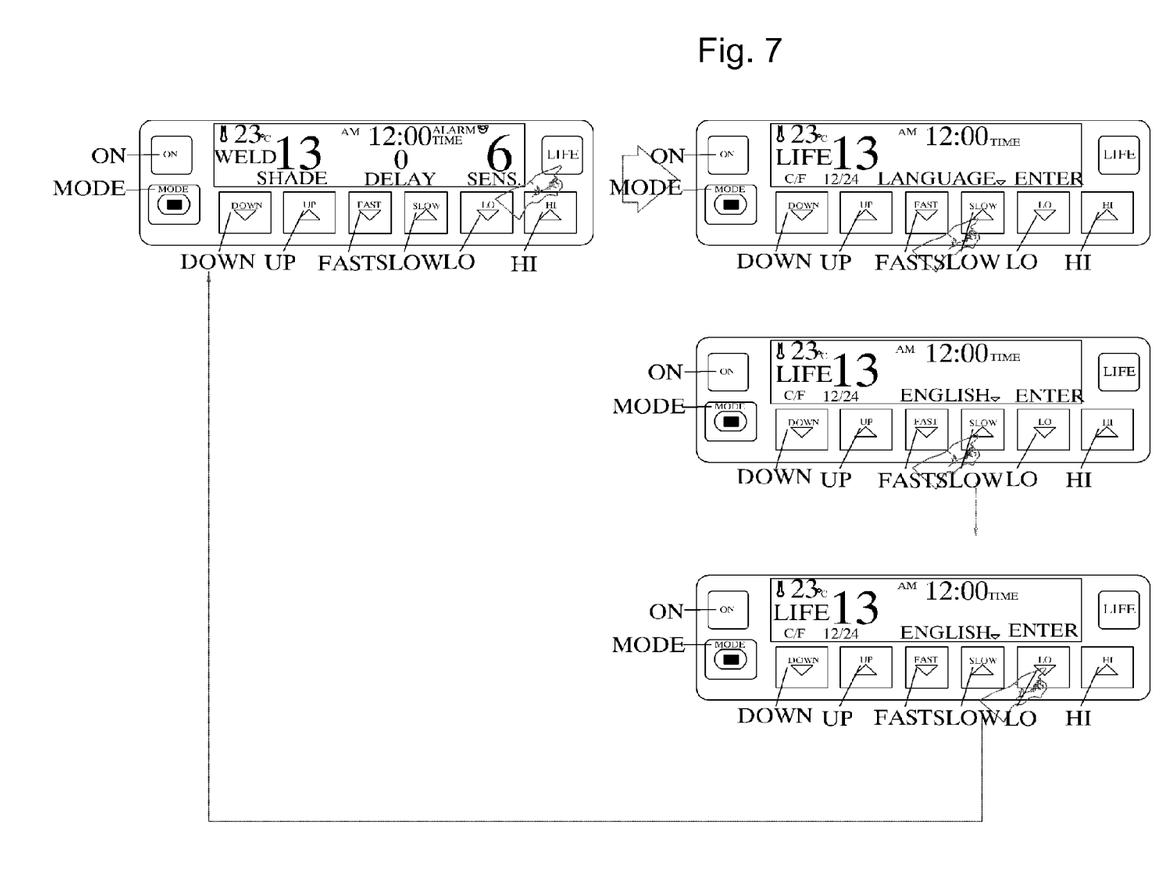
FIG. 7 illustrates a procedure for selecting and using the user's own language according to a preferred embodiment of the present invention.

FIG. 7 illustrates a procedure for providing information in the user's own language when the user uses the welding helmet cartridge according to the present invention.

At an initial step S210, when the user presses the "LIFE" button, the controller 250 enters a life mode entrance step S220. At the life mode entrance step S220, the user may select a 12/24 time mode selection item, a Fahrenheit/Celsius selection item, an alarm adjustment item, and a time adjustment item. Here, when the user again presses the "LIFE" button, the word "LANGUAGE" is displayed to allow the user to select a language. The user then presses an arrow button of the displayed letter "LANGUAGE" to select one of the languages Korean, English, French, German, Italian, Chinese, Japanese, Russian, Arabic, Greek, Brazil, Thai, and Vietnamese. When the user presses the enter key after selecting the language, the language of information displayed on the display unit 230 is converted into the selected language and the procedure is then completed.

Since task details described above with reference to FIGS. 4 to 7 are also displayed in multiple languages, the present invention has an advantage in that even workers who do not know languages of other countries can read the displayed task information in their own language and thus can work conveniently. While all welding helmet cartridges are currently designed to display task information in English, the present invention eliminates the need to design welding helmet cartridges which display task information in the language of each country to which the welding helmet cartridges are exported. In addition, non-English speaking workers in the United States can select their own language for display of &&task information when using the welding helmet cartridges.

The present invention also has an advantage in that the welding helmet cartridge recognizes voice of a user to determine the user's own language so that the welding helmet cartridge displays operating states (or task information) in the user's own language without manual control by the user.

Figure 8:
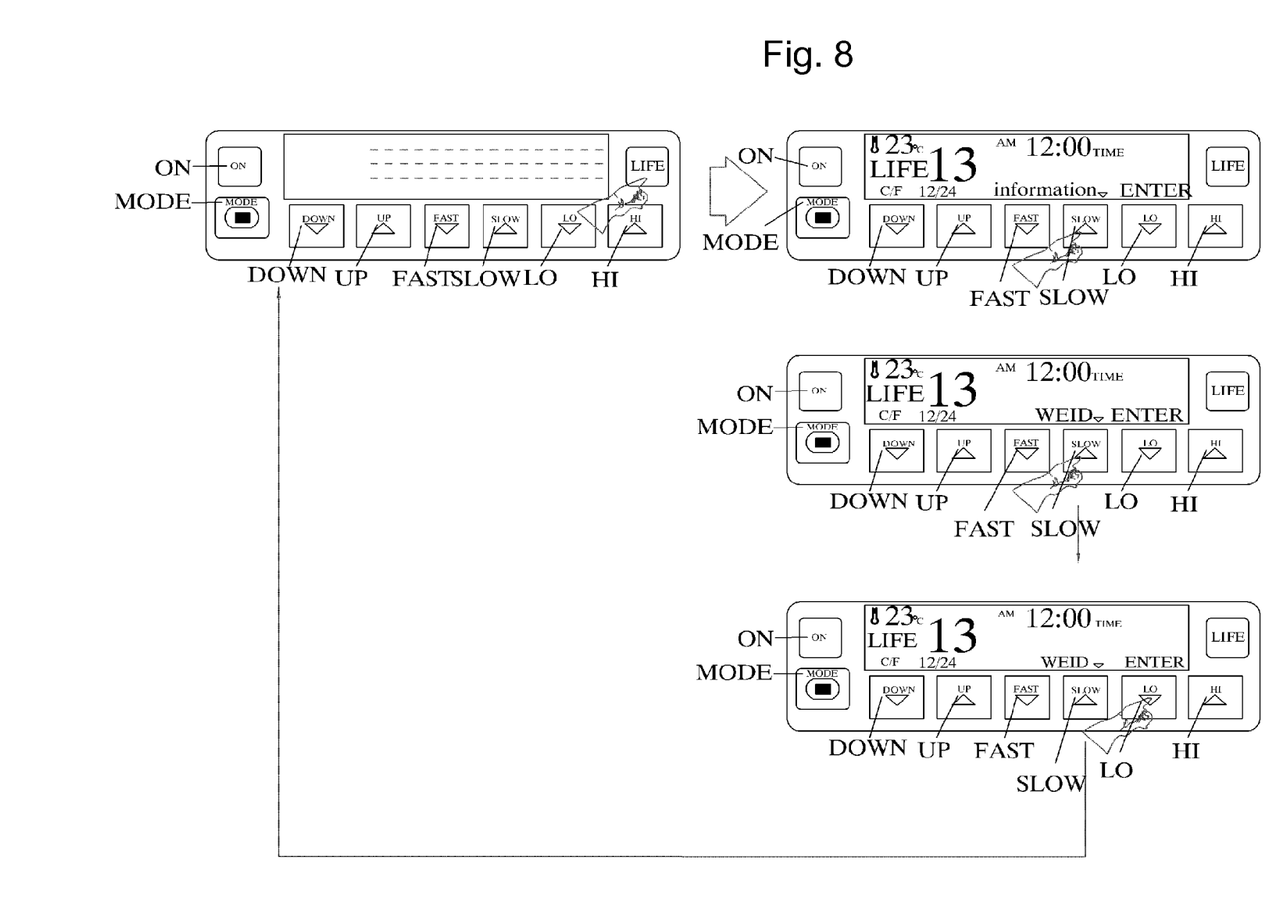
FIG. 8 illustrates a procedure for providing information such as a user manual to the user in the cartridge according to a preferred embodiment of the present invention.

FIG. 8 illustrates a procedure for providing information such as a user manual to the user in the cartridge according to the present invention.

If the user of the welding helmet presses the "LIFE" button for a long time or presses a guide button (denoted by "information" in FIG. 8) at an initial step S210, the welding helmet cartridge displays guide information in each selected language. Information of a welding task "WELD", a cutting task "CUTTING", a grind task "GRIND", and an X-mode task "X-MODE" are selectively or sequentially displayed. When the user presses an arrow button of a displayed word "LANGUAGE" to select a desired language, the displayed information is converted into information of the selected language so that information of each displayed term such as "WELD", "CUTTING", "GRIND", and "X-MODE" is displayed in the selected language.

As is apparent from the above description, the present invention has a variety of advantages. For example, the cartridge not only shields a worker's face from light generated when the worker performs a task such as welding or cutting but also automatically performs shade level adjustment and work time setting functions for each task, and also allows information such as an operating status, a user manual, and relevant terms to be displayed in multiple languages on the cartridge, thereby increasing convenience of task. While all welding helmet cartridges are currently designed to display task information in English, the present invention eliminates the need to design welding helmet cartridges which display task information in the language of each country to which the welding helmet cartridges are exported. In addition, non-English speaking workers in the United States can select their own language for display of task information when using the welding helmet cartridges.

In addition, the cartridge recognizes voice of a user to determine the user's own language so that the welding helmet cartridge displays operating states (or task information) in the user's own language without manual control by the user.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for controlling a cartridge of a welding helmet, the method comprising: sequentially performing a welding step, a cutting step, a grinding step, and an X-mode step automatically according to a preset condition, a shade level of an LCD screen, and an operating time of the cartridge, wherein the cartridge includes the LCD screen, a display unit, a controller, and a memory;
    calculating, by the controller, a work time during which the LCD screen of the cartridge is darkened and storing the calculated work time in the memory and displaying the stored work time on the display unit when entering a life mode entrance step, and
    storing data of an operating state in multiple preset languages in the memory and displaying data of the operating state in one language, which the controller has selected from among the multiple preset languages, on the display unit,
    wherein the cartridge further includes a voice recognition unit for recognizing voice of a user, and
    wherein the controller determines a language recognized by the voice recognition unit and selects data of an operating state of the recognized language stored in the memory and displays the data of the operating state of the recognized language on the display unit.

2. The method according to claim 1, wherein the memory stores data of at least one language so that data of the selected language is displayed on the LCD screen.

3. The method according to claim 1, further comprising:
    selecting one of a 12/24 time mode selection item, a Fahrenheit/Celsius selection item, an alarm adjustment item, and a time adjustment item by the user at the life mode entrance step,
    proceeding, by the controller, to a time setting step at which the user adjusts hour and minute values when the user selects the alarm adjustment item,
    completing time setting when the user presses an enter key at a time setting completion step,
    proceeding, by the controller, to a work time check step at which the user checks a work time when the user selects an accumulated time item at the life mode entrance step,
    proceeding, by the controller, to a time adjustment step at which the user again adjusts hour and minute values when the user selects the time adjustment item, and
    completing time adjustment when the user again presses the enter key at the time setting completion step.

4. The method according to claim 1, wherein a language of information to be read and displayed from the memory, which stores information in at least one language, is selected and set.

5. The method according to claim 1, wherein the display unit immediately displays a work time when the controller enters the life mode to save power consumption.

6. The method according to claim 1, wherein information of a welding task "WELD", a cutting task "CUTTING", a grind task "GRIND", and an X-mode task "X-MODE" are selectively or sequentially displayed in at least one language.

* * * * *